United States Patent
Rezzonico et al.

(10) Patent No.: US 7,725,158 B2
(45) Date of Patent: May 25, 2010

(54) APPARATUS FOR MAGNETIC RESONANCE IMAGING

(75) Inventors: Fabio Rezzonico, Como (IT); Orfeo Contrada, Genoa (IT)

(73) Assignee: Esaote, S.p.A., Casale Monferrato (IT)

( * ) Notice: Subject to any disclaimer, the term of this patent is extended or adjusted under 35 U.S.C. 154(b) by 487 days.

(21) Appl. No.: 10/886,695

(22) Filed: Jul. 9, 2004

(65) Prior Publication Data

US 2005/0033155 A1   Feb. 10, 2005

Related U.S. Application Data

(60) Provisional application No. 60/486,240, filed on Jul. 11, 2003.

(51) Int. Cl.
*A61B 5/05* (2006.01)
*A47B 13/00* (2006.01)

(52) U.S. Cl. .......................... 600/415; 5/601
(58) Field of Classification Search ............... 600/410, 600/407, 415, 425; 5/601, 621, 622, 624
See application file for complete search history.

(56) References Cited

U.S. PATENT DOCUMENTS

| | | | |
|---|---|---|---|
| 4,875,485 A | | 10/1989 | Matsutani et al. |
| 4,964,793 A | * | 10/1990 | Antosh .................. 425/62 |
| 5,779,637 A | | 7/1998 | Palkovich et al. |
| 5,903,940 A | * | 5/1999 | Volker et al. ............... 5/611 |
| 6,456,684 B1 | * | 9/2002 | Mun et al. .................. 378/20 |
| 7,057,389 B2 | * | 6/2006 | Kamimura et al. ......... 324/318 |
| 2001/0003789 A1 | * | 6/2001 | Dutto et al. ............... 600/415 |

FOREIGN PATENT DOCUMENTS

| | | |
|---|---|---|
| DE | 199 23 947 A1 | 12/2000 |
| EP | 0 927 889 A2 | 7/1999 |
| EP | 1 027 862 A1 | 8/2000 |
| WO | WO 03/041578  * | 5/2003 |

* cited by examiner

*Primary Examiner*—Brian Casler
*Assistant Examiner*—Elmer Chao
(74) *Attorney, Agent, or Firm*—Buchanan Ingersoll & Rooney PC

(57) ABSTRACT

An apparatus for MRI (Magnetic Resonance Imaging) includes a scanner, a support for a patient, and a supporting bench for the scanner and for the patient support, wherein the scanner and said patient support are mounted on the supporting bench such that a position of at least one of the scanner and the patient support can be changed with respect to the other of the scanner and the patient support.

20 Claims, 8 Drawing Sheets

Fig. 2
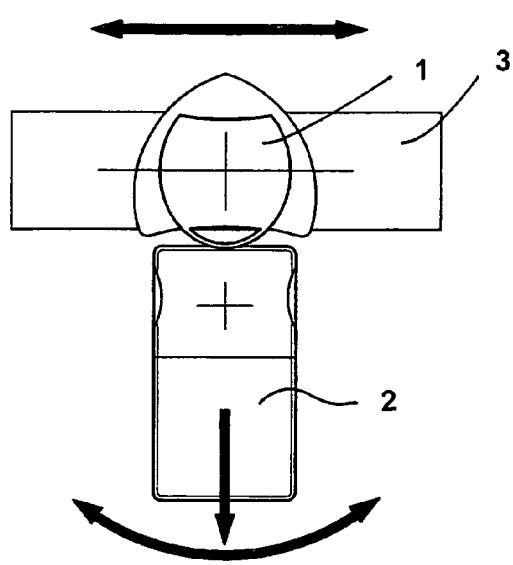
Fig. 3
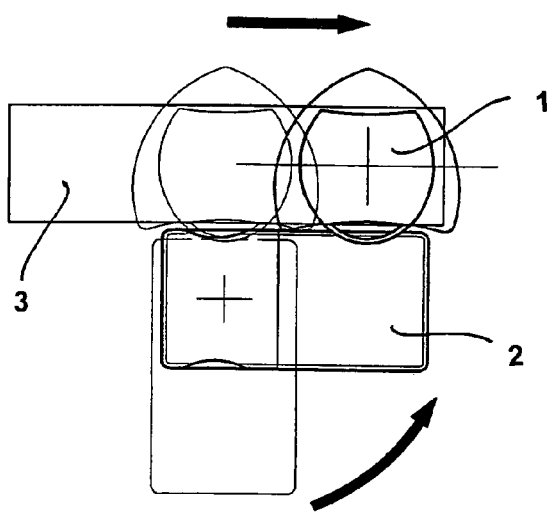
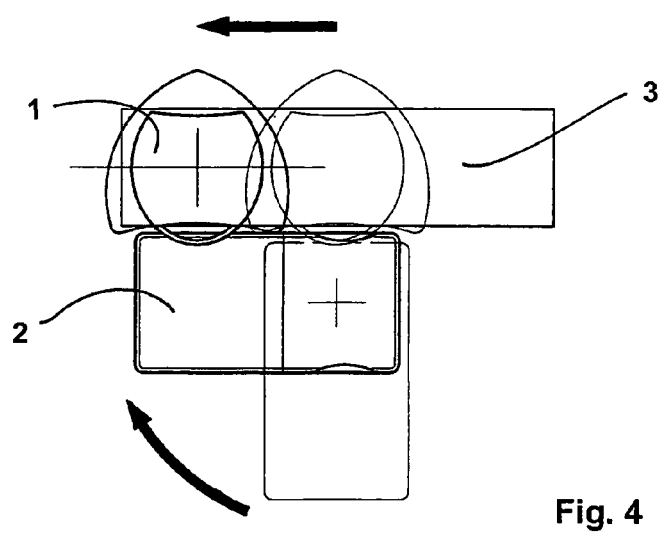
Fig. 4

APPARATUS FOR MAGNETIC RESONANCE IMAGING

CROSS-REFERENCE TO RELATED APPLICATIONS

This application claims the benefit of U.S. Provisional Application Ser. No. 60/486,240, which was filed on Jul. 11, 2003, the entire contents of which is hereby incorporated herein by reference.

BACKGROUND OF THE INVENTION

The invention relates to an apparatus for MRI (Magnetic Resonance Imaging) including a scanner, a support for the patient, and supporting benches for supporting the scanner and the patient.

It is well known from prior art to make a Magnetic Resonance Imaging apparatus comprising means for supporting the patient in different ways, and having one or more degrees of freedom with respect to the scanner. It is also well known from prior art to use means for supporting and moving the scanner itself with respect to the room where the examination takes place and with respect to the patient himself. Prior art apparatus have some problems as regards the correct positioning of the patient: the patient often has to take unnatural positions during the examination in order to examine a particular part of his body, and he needs to be repositioned to scan the different body parts in the correct way. Especially in prior art MRI apparatus wherein the scanner is free to move with respect to the patient support, the examination needs a frequent and time-wasting initial phase of positioning, since the medical staff has to set the position of the scanner and the patient support in such a way to obtain the best results in imaging the part of the patient body under examination.

Moreover, prior art apparatus with the scanner joined to the patient support are often not optimized, since the volume that is used is larger than the necessary volume, this leads to have an examination room larger than necessary.

Particularly in known MRI apparatus there is often a part of the examination room whose function is to contain the data processor and its related devices for processing data and displaying results, as well as the control unit, i.e., the electric/electronic devices for controlling the scanner and the patient table motion. This fact leads to a non-optimal space management since a large part of the room is used to contain such devices.

Moreover, it has been found in prior art apparatus that there is another area that is not used, i.e., the area under the patient support and the area under the scanner. Usually in known apparatus two different benches are provided, one for supporting the scanner and one for supporting the patient support, both of them are made in such a way so that they can be used for supporting the scanner or the patient support. Even in the prior art apparatus wherein the scanner is moved together with the patient support, the benches are different, and their only function is to move the scanner and the patient support in their respective correct positions, in this case in fact they always include only means for moving, such as electric engine, guides and so on.

In the case of separated benches for individually supporting the scanner and the patient support that have to be moved together there is another problem, they need some lines to transmit the signals from the control unit from/to the scanner, from the control unit from/to the patient support, and from the scanner itself to/from the displaying devices and from/to all of the said elements, and this causes dedicated lines, that must be usually positioned under the wall or under the floor, having the evident drawback that they raise when the apparatus has to be moved or installed from a room to another dedicated one.

OBJECTS AND SUMMARY

An object of the invention is to provide an MRI apparatus that is able to overcome said disadvantages above mentioned.

This will be achieved by an embodiment of the invention in which said scanner and said patient support are mounted with at least one degree of freedom on one and the same supporting bench.

This leads to some specific advantages, that will solve the above mentioned problems related to the prior art.

First of all the fact that the scanner and the patient support are mounted together on the same bench allows an important reduction of the used volume, and the above mentioned problem regarding the line is also solved: the lines from the scanner to/from the patient support are located inside the bench itself, this causes less problems when installing or moving the MRI apparatus from/to another room, in fact the above mentioned lines are internal to the bench, being not necessary to locate them under the floor or the walls.

Moreover, the embodiment according to the present invention has a height from ground substantially equal to the height of patient support from ground minus the thickness of the patient support itself, and this is an important advantage, because the substantially rounded external shape of the bench, in combination with its height leads to a kind of bench that is not particularly wide, but at the same time it is sufficient for containing all the means for moving and positioning the scanner and the patient support. Moreover, the supporting bench embodiment of the present invention allows the patient to stand still during the examination, since the internal part of the scanner examination cavity where the patient uses to lay his body part under examination is substantially as the same height of the patient himself, in such a way that the patient stands in an examination position and he is not under physical stress and he can stand still during the examination process.

The invention addresses further improvements, which form the subject of the dependant claims.

BRIEF DESCRIPTION OF THE DRAWINGS

The features of the invention and the advantages derived therefrom will appear more clearly from the following description of some embodiments by way of example, illustrated without limitation in the accompanying drawings, in which:

FIGS. 2, 3 and 4 are top plan views of the possible motions of the invention embodiment of FIG. 1

DETAILED DESCRIPTION OF THE PREFERRED EMBODIMENTS

Figure 1:
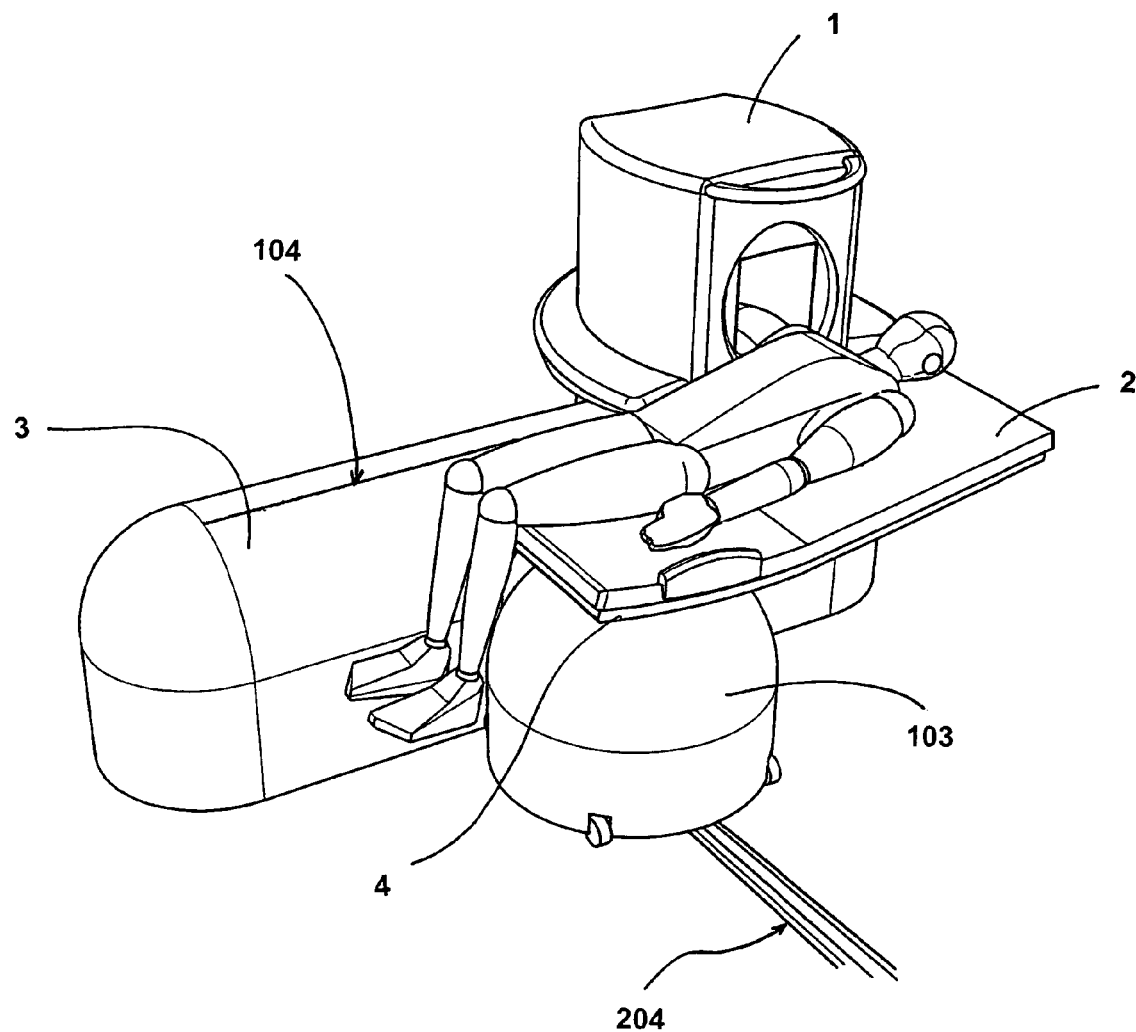
FIG. 1 is a perspective view of a first embodiment of the invention wherein the bench (3) of the invention has an external substantially rounded shape, and its overview shape is a T-shape.

The first embodiment of FIG. 1 relates to a particular bench 3 according to the present invention wherein the external shape of the bench 3 itself is a substantially rounded shape, moreover in this embodiment the bench 3 has an overview T-shape: the scanner 1 is mounted over the elongated part of the T-shaped bench 3 while the patient support 2 is mounted on a different part of the bench which is perpendicular to the elongated part in such a way to form an overview T-shape. The patient support bench 103 of the patient support 2 is mounted on a guide 204 which allows it to move along said guide 204. The scanner 1 is mounted on a scanner guide 104 which, in this particular embodiment, is perpendicular to the patient support guide 204, and said scanner guide 104 is mounted on the top and along the longitudinal extension of the bench 3. Between the scanner 1 and the patient support 2, known guides 4 for rotation/translation are provided in order to achieve the possible motions of FIGS. 2, 3 and 4, which guides 4 are positioned between the patient support 2 and the patient support bench 103 and between the scanner 1 and the scanner guide 104 and between the patient support bench 103 and the patient support guide 204. Thus it is possible to obtain the motions and the different examination positions illustrated in FIGS. 2, 3 and 4. Particularly FIG. 2 illustrates the examination position for patient leg: in this figure the scanner 1 is positioned in the middle of the bench 104 and stands in front of the patient support 2, allowing the patient to introduce in the scanner cavity his lower part of the body. Moreover, thanks to the above mentioned guide for rotation/translation, it is possible to move the scanner 1 along the bench 3, as shown by black arrows, while positioning the patient support 2 by rotating and/or translating the patient support 2 itself, as shown by black arrows. Thus it is possible to position even patients that can not move their legs, by positioning the patient himself on the patient support 2 and then rotating the patient support in position, i.e., perpendicular to the bench 3, and then translating the patient support in direction of the scanner, in such a way that the patient is able to introduce the leg to be examined into the examination cavity of the scanner 1 itself. By moving the scanner 1 along the bench 3 it is possible to position the scanner and the scanner examination cavity over the left or right leg of the patient. In FIGS. 3 and 4 are illustrated the positions of the patient support 2 and the scanner 1 along the bench 3 for arm/shoulder examination. Particularly, FIG. 3 shows the position for right arm/shoulder examination and FIG. 4 for left arm/shoulder examination. In FIGS. 2, 3 and 4 it can be clearly seen that the volume that is used for the different apparatus positions is not bigger than the length of the bench 3 itself and not bigger than the length of the patient support, this allows a space-saving, as said above.

Furthermore FIGS. 1, 5, 9, and 12 clearly show that the bench 3, 303, 403, 503 has an height from ground substantially equal to the height of the patient support 2, 302, 402, 502 from ground minus the thickness of the patient support 2, 302, 402, 502 itself, and/or an height from ground substantially equal to the height of patient support 2, 302, 402, 502 from ground minus the thickness of the lower part of the scanner examination cavity. This is a great advantage, in fact such height is useful in order to position the patient under examination in a comfortable way, allowing the patient to rest during the examination in a steady position, leading to a better and shorter imaging process.

It will be noticed in FIG. 1 that the total height of the patient support bench 103 corresponds to the height of the bench 3, and it is possible to remove the patient support guide 204, having a T-shaped fixed bench, where the patient support bench 103 is simply a perpendicular extension of the main bench 3.

The positioning illustrated in FIGS. 2, 3 and 4 are only examples of the possible positioning between the bench 3 and the patient support 2; moreover the positioning may be manual or may be driven by electric/electronic devices not shown in figures, being known art.

Furthermore in the above figures there are not illustrated the above mentioned rotating/translating devices, the same being obvious for the person skilled in the art.

Figure 5:
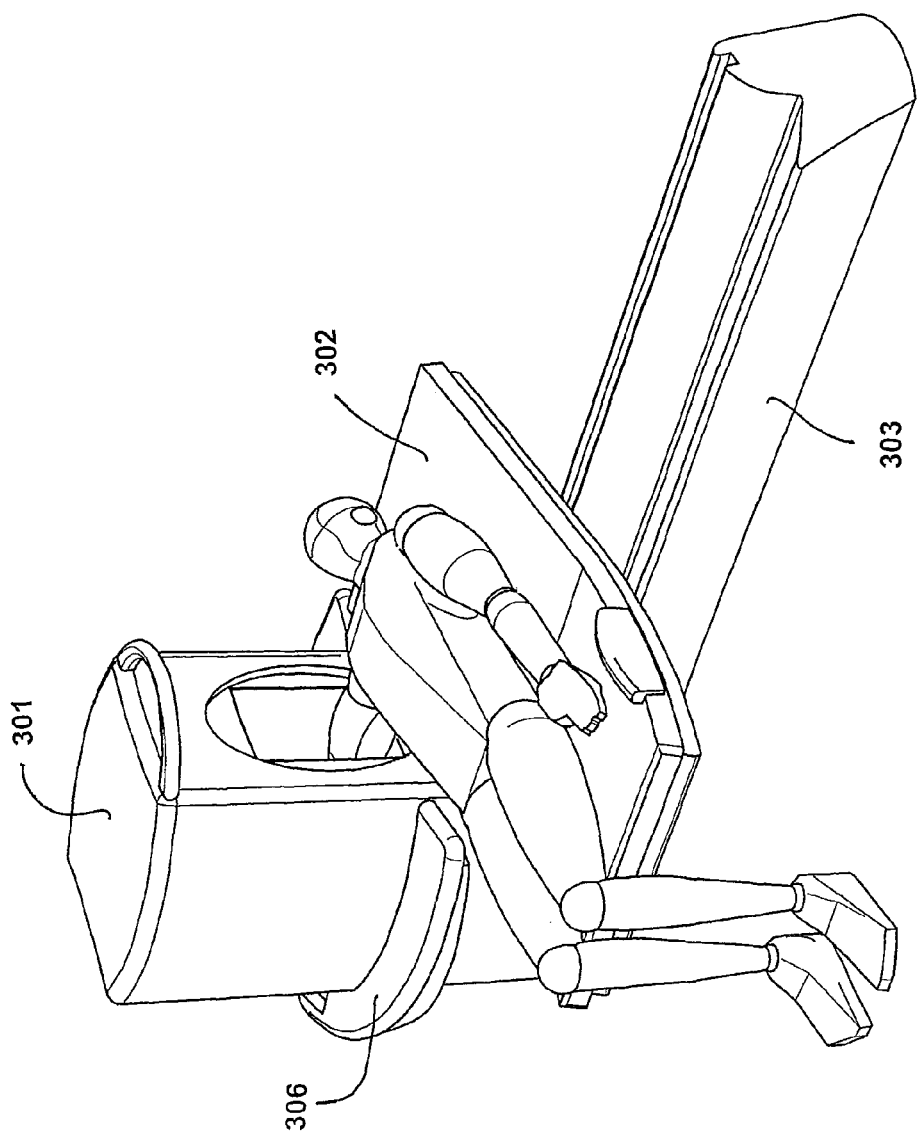
FIG. 5 is a perspective view of a second embodiment of the invention wherein the bench (3) of the invention has a different symmetrical external shape.

In FIG. 5 is illustrated another preferred embodiment of the invention, wherein the bench 303 has only a longitudinal extension, but having a particular cross section. In this preferred embodiment the scanner 301 is secured at one end of the bench 303 in side position with respect to the longitudinal extension of the bench 303 itself, while the patient support 302 can rotate and/or translate along the bench 303 in order to introduce the patient part under examination inside the examination cavity of the scanner. It should be noted from FIGS. 6 and 7 that the patient support 302 may translate and rotate along the bench 303 in the direction illustrated by black arrows. This leads to a short examination apparatus in which the T-shape figured out in FIG. 1 is not necessary, and in which the scanner 1 itself is fixed. In this case the advantages are that the whole space that has been used is even less than the space used in the apparatus shown in FIG. 1, and the electric/electronic driving for the positioning is easier. In this case it is possible also to have manual driving means that are easy to use and simple to make. Even in this case, as in embodiments shown in FIGS. 1, 9 and 12, it is evident that the height of the bench is optimal for positioning the patient on the patient support, in fact, the height of patient support is the normal sitting height for a person, this leading to a comfortable movements for the patient, moreover, by using the bench 303 according to the invention, the heights of the scanner 301 and the patient support 302 with respect with each other, allow the patient body parts under examination to lay in a comfortably position for the patient itself.

Figure 8:
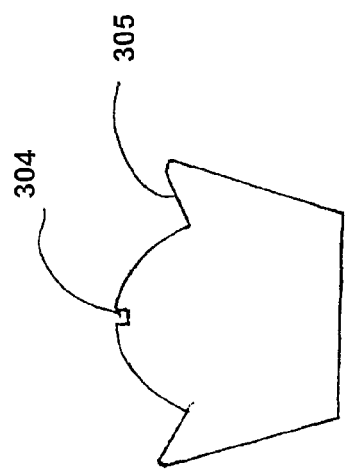
FIG. 8 is a cross sectional view of the bench of FIG. 5.
Figures 6, 7:
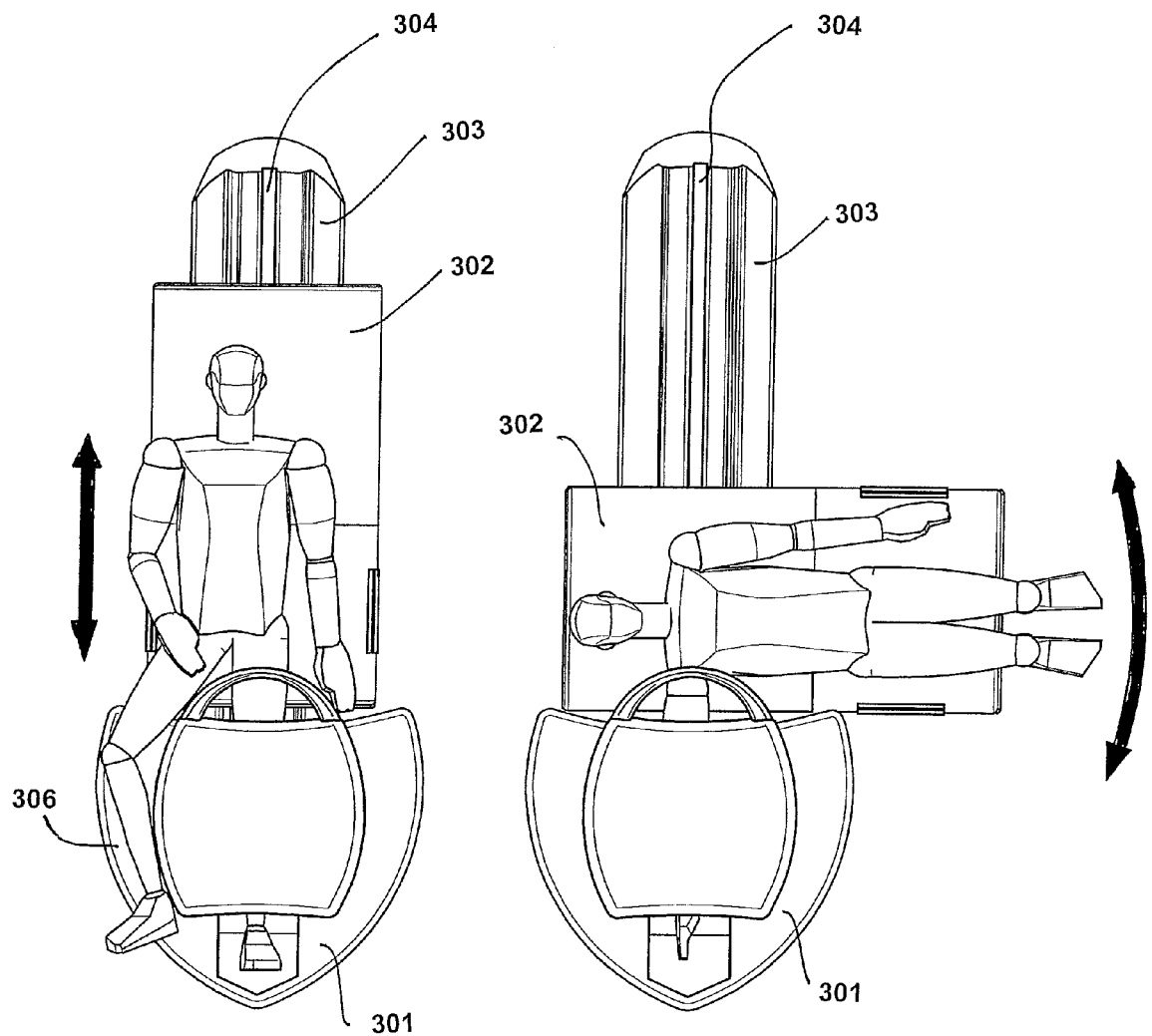
FIGS. 6 and 7 are top plan views of two possible motions of the invention embodiment of FIG. 5.

In FIGS. 6 and 7 are shown the different positioning for leg/foot examination and arm/shoulder examination respectively, obtained by the rotation/translation of the patient support 302 along the patient support guide 304 positioned on the top of the bench 303, as shown also in FIG. 5. In this particular preferred embodiment the bench 303 has a particular symmetrical cross section, shown in FIG. 8. this cross section shows a central arched part ending on both sides with two supporting wings 305 forming each one a lateral groove. Each wing 305 starts from the ending lateral edge of the arched part and has a planar surface in this preferred embodiment, the arched part ends at his center at an upper level with respect to the two wings. In FIG. 8 it will be also noted that the patient support guide 304 is positioned at the top of the bench 303 and it will be noted also the particular supporting wings 305 of this particular bench 303; this supporting wings 305 may be very useful in case of heavy patients and in all that cases when it is necessary to have a strong and well fixed structure for the patient support. In FIGS. 5, 6 and 7 the patient support itself is represented by a seat with a movable back, being possible to use also a table, and being possible also to use a movable scanner as shown in FIGS. 1, 2, 3, 4. In addition, the lateral external wall of the scanner 301 includes a peripheral limb rest 306 for supporting the arm or leg not being scanned, as shown best in FIG. 6 wherein limb rest 306 is cantilevered from the scanner and supports one of the patients leg.

Figure 9:
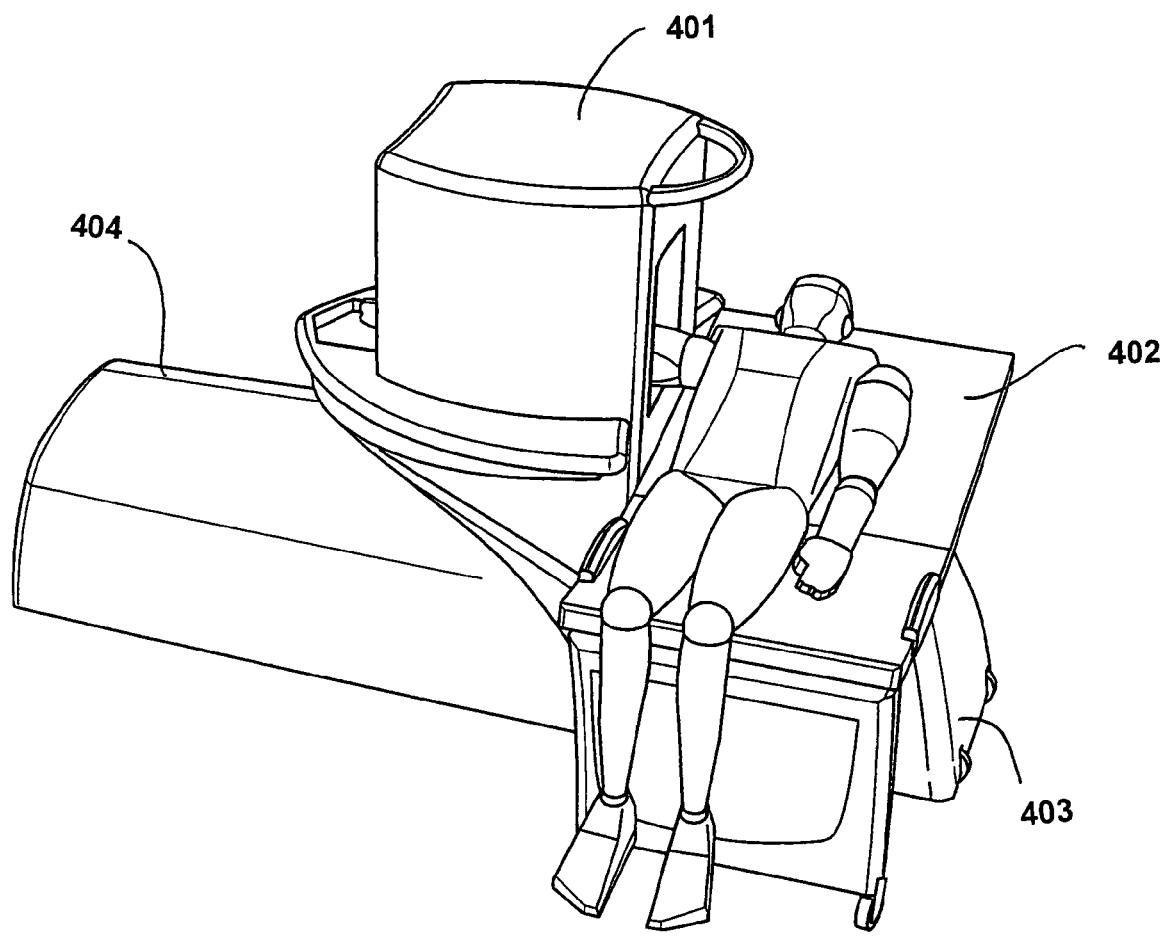
FIG. 9 is a perspective view of a third embodiment of the invention in which the bench (3) of the invention has an external rounded shape and its overview shape has only a longitudinal extension.

In FIG. 9 it is shown another preferred embodiment of the invention wherein the bench 403 has a external rounded shape, as shown and disclosed for FIGS. 1, 2, 3, 4, but in FIG. 9 the overview shape of the bench 403 itself has only a longitudinal extension, as shown and disclosed for FIGS. 5, 6, 7, 8. In this particular embodiment of the invention the scanner 401 may translate along the bench 403 by using a scanner guide 404, while the patient support 402 is secured at one end of the bench 403 and may only rotate about its vertical axis. In this case the supporting bench 403 has a rounded cross section, as said above, since the scanner is often less heavy than the patient support with the patient himself, and there is no need of a supporting shape in order to have a well fixed structure. This leads to a less expensive apparatus but also a less strong apparatus than the one shown in FIGS. 5, 6, 7, and 8.

Figures 10, 11:
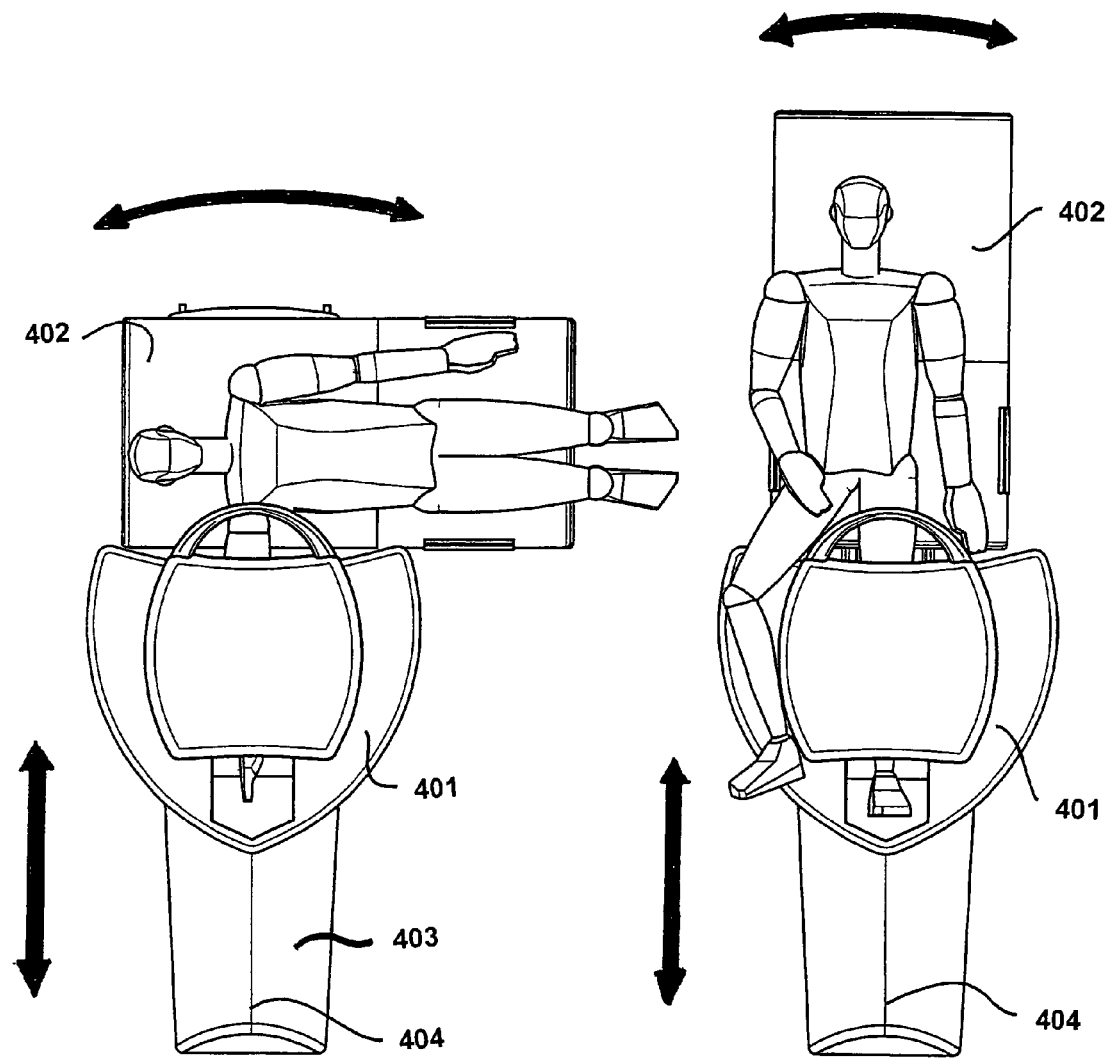
FIGS. 10 and 11 are top plan views of two possible motions of the invention embodiment of FIG. 9.

In FIGS. 10 and 11 are illustrated the examination positions for arm/shoulder and leg/foot respectively. In FIGS. 10 and 11 the scanner 401 may translate along the scanner guide 404 as shown by black arrows, and the guide 404 is positioned as usual at the top of the bench 403. In this case the scanner has only means for translating along the bench, while the patient support may rotate only with respect to its vertical axis as shown by black arrows on the top of the drawings. In this case it is evident that the means for rotating the patient support 402 is only a rotational guide positioned under the patient support 402 itself and over the bench 403. From a comparison between FIG. 6 and FIG. 11 it is evident that the embodiment of FIG. 6 takes less space than the embodiment of FIG. 11 but, as said before, the simple shape of the bench of the embodiment shown in FIG. 11 is cheaper. Thus it is possible to choose the best configuration of the bench for the examination room in use. It is possible also to combine the two solutions illustrated in FIGS. 5 and 9 in order to have a bench where it is possible to rotate/translate the scanner and the patient support, this is a more versatile but more expensive solution. The supporting bench 403 of FIG. 9 achieves all the advantages disclosed for the supporting bench of FIGS. 1 and 5 and related to the comfortable positioning of the patient and of the part of the patient under examination.

Figure 12:
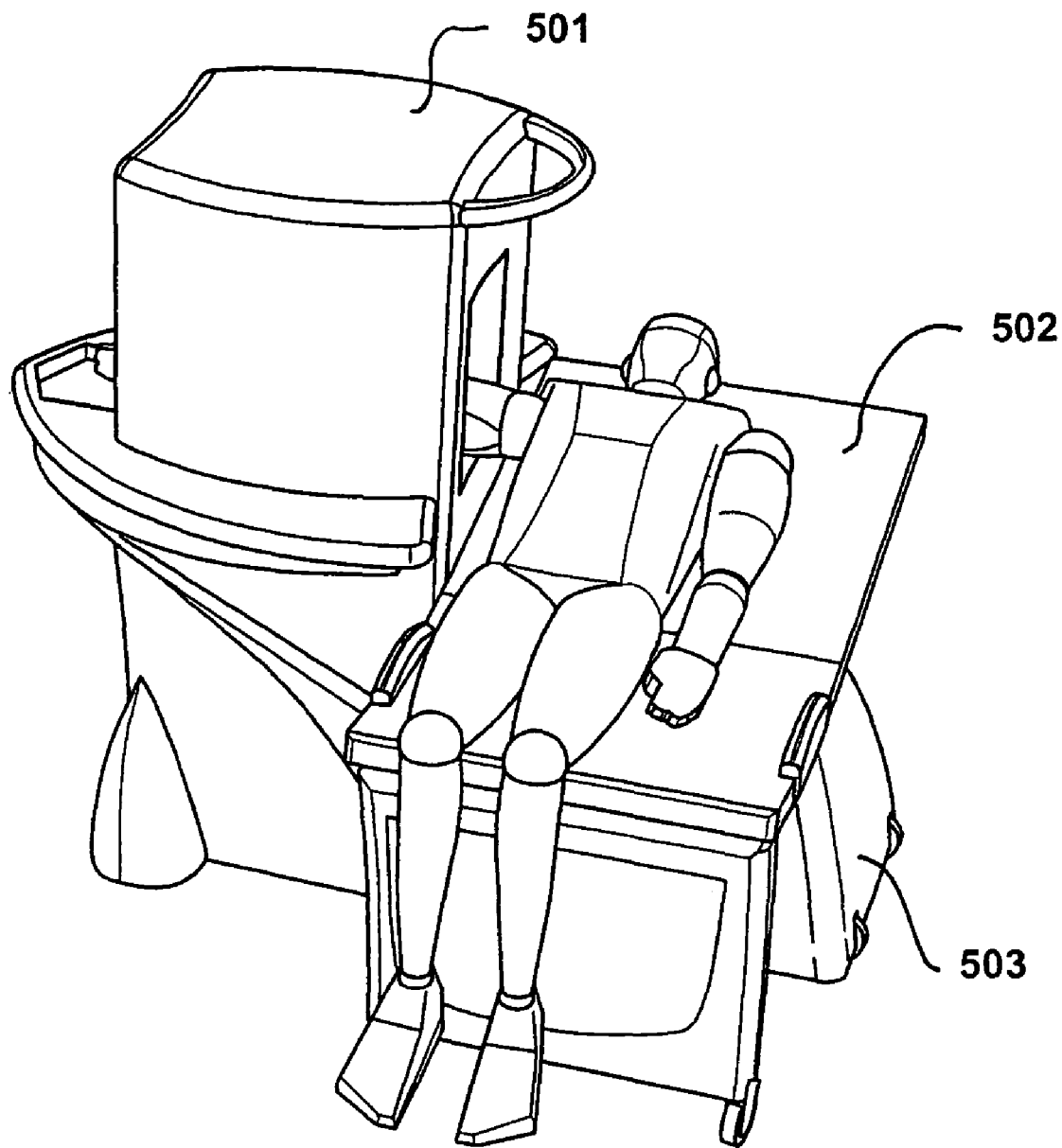
FIG. 12 is a perspective view of a fourth embodiment of the invention wherein the bench (3) of the invention has an external rounded shape and its overview shape has only a limited longitudinal extension.
Figure 13:
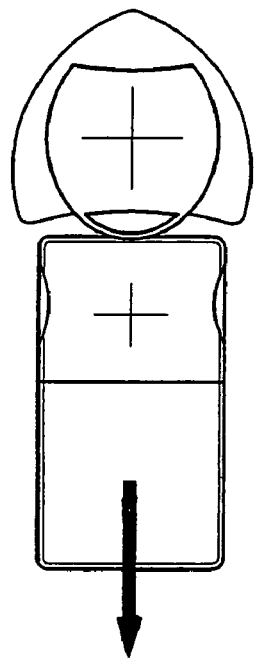
FIGS. 13, 14, and 15 are top plan views of different motions of the invention embodiment of FIG. 12.
Figure 15:
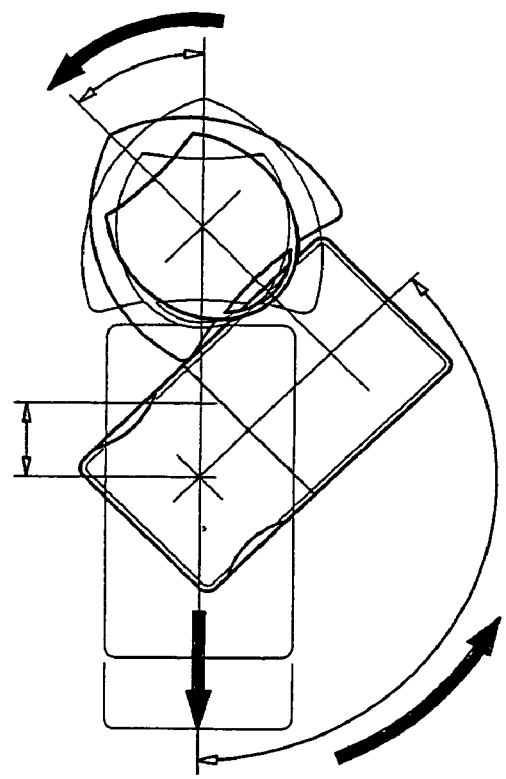
Figure 14:
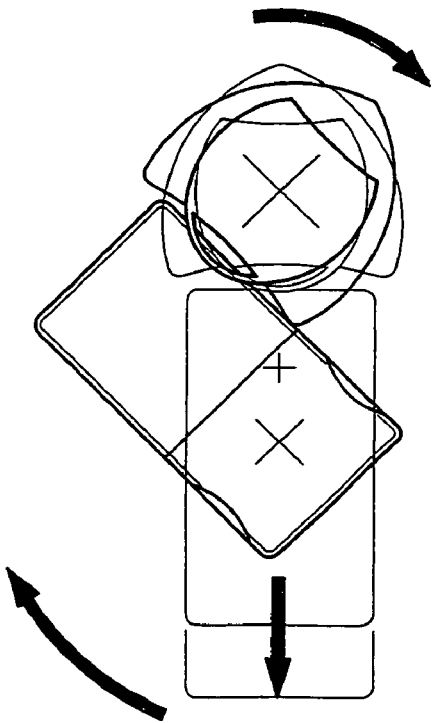

The fourth preferred embodiment is illustrated in FIG. 12. In this case the supporting bench 503 has a longitudinal extension substantially equal to the length of the scanner 501 plus the width of the patient support 502, while the supporting bench 503 has the same height as disclosed above, achieving the same advantages for the patient comfortable positioning related matter. In the preferred embodiment of FIG. 12, the patient support 502 can rotate along a guide while the scanner can rotate about its vertical axis in order to introduce the patient part under examination in the examination cavity of the scanner. It is evident from FIGS. 13, 14, 15 that the scanner 501 and the patient support 502 work together in order to achieve the right position. In particular in FIG. 13 is shown the position for leg/foot examination, in FIG. 14 is shown the position for left arm/shoulder examination, in FIG. 15 is shown the position for right arm/shoulder examination. It is evident that the present embodiment reduces a lot the space used to position the patient under examination in the examination room. This embodiment achieves the same advantages disclosed before for FIGS. 1 to 11.

In all the embodiments presented in FIGS. 1 to 15 the supporting bench 3, 303, 403, 503 may have an internal volume that can be used to locate all or at least part of the electric/electronic driving control and/or the electric/electronic apparatus for processing and generating images, this leading to a space saving, that may be useful when the examination room is a small one. Moreover, in all these embodiments it is possible to mount directly on the supporting bench an imaging unit, with a video and an operator seat and all the imaging and driving control in order to position and to execute the examination, this leading to a further space saving.

Furthermore, it should be noted that in these last cases, in which the driving apparatus and/or the controls for driving, for examination, and for imaging are mounted on a single bench, there is no need to use lines located under the walls or under the floor, being necessary only to have an electric line that leads the main power supply to the MRI apparatus.

Although only preferred embodiments are specifically illustrated and described herein, it will be appreciated that many modifications and variations of the present invention are possible in light of the above teachings without departing from the spirit and intended scope of the invention.

The invention claimed is:

1. An integrated apparatus for MRI (Magnetic Resonance Imaging) comprising:
   a scanner,
   a support for a patient, and
   a supporting bench fully supporting a weight of both the scanner and the patient support,
   wherein said scanner and said patient support are mounted on said supporting bench such that a position of at least one of the scanner and the patient support can be changed with respect to the other of the scanner and the patient support, and
   wherein said supporting bench has a cross section that is in a form of a central arched part ending on both sides with two supporting wings, each one of said wings forming a lateral V-shaped groove having opposing upwardly projecting sides, each wing starting from a terminal lateral edge of the arched part and having a planar surface, a center peak of said arched part defining an upper level above the upwardly projecting side of the two wings.

2. The apparatus for MRI (Magnetic Resonance Imaging) according to claim 1, wherein at least one line that leads a power supply to the MRI apparatus is housed in the supporting bench.

3. The apparatus for MRI (Magnetic Resonance Imaging) according to claim 1,
   wherein said supporting bench has an internal volume for locating all or at least part of an electric/electronic driving control and/or an electric/electronic apparatus for processing and generating images.

4. The apparatus for MRI (Magnetic Resonance Imaging) according to claim 1, wherein said supporting bench has a height from ground substantially equal to a height of the patient support from ground minus the thickness of the patient support itself.

5. The apparatus for MRI (Magnetic Resonance Imaging) according to claim 4, wherein said scanner has two degrees of freedom with respect to said supporting bench.

6. The apparatus for MRI (Magnetic Resonance Imaging) according to claim 5, wherein said scanner is mounted on said supporting bench by means for rotating and/or translating with respect to said supporting bench.

7. The apparatus for MRI (Magnetic Resonance Imaging) according to claim 6, wherein rotation of said scanner is made about a vertical axis.

8. The apparatus for MRI (Magnetic Resonance Imaging) according to claim 6, wherein translation of said scanner occurs along one or two horizontal axis, the first of which is parallel with respect to the length of said supporting bench and the second axis is perpendicular with respect to the first one.

9. The apparatus for MRI (Magnetic Resonance Imaging) according to claim 6, wherein said means for rotation/translation provided on said scanner are electrically/electronically controlled.

10. The apparatus for MRI (Magnetic Resonance Imaging) according to claim 6, wherein rotation and translation of said scanner support are carried out simultaneously.

11. The apparatus for MRI (Magnetic Resonance Imaging) according to claim 4, wherein in that said patient support has two degrees of freedom with respect to said supporting bench.

12. The apparatus for MRI (Magnetic Resonance Imaging) according to claim 4, wherein said patient support is mounted on said supporting bench by means for rotating/translating with respect to said supporting bench.

13. The apparatus for MRI (Magnetic Resonance Imaging) according to claim 12, wherein said rotation of said patient support is made about a vertical axis.

14. The apparatus for MRI (Magnetic Resonance Imaging) according to claim 12, wherein said translation of said patient support occurs along one or two horizontal axis, the first of which is parallel with respect to the length of said supporting bench and the second axis is perpendicular with respect to the first one.

15. The apparatus for MRI (Magnetic Resonance Imaging) according to claim 12, wherein said means for rotation/translation provided on said patient support are electrically/electronically controlled.

16. The apparatus for MRI (Magnetic Resonance Imaging) according to claim 12, wherein rotation and translation of said patient support are carried out simultaneously.

17. The apparatus for MRI (Magnetic Resonance Imaging) according to claim 1, wherein said supporting bench has two different guides for rotating and/or translating said patient support and said scanner.

18. The apparatus for MRI (Magnetic Resonance Imaging) according to claim 1, wherein said supporting bench has a height from ground substantially equal to a height of the patient support from ground minus a thickness of a lower part of an examination cavity of the scanner.

19. The apparatus for MRI (Magnetic Resonance Imaging) according to claim 18, wherein said scanner has two degrees of freedom with respect to said supporting bench.

20. The apparatus for MRI (Magnetic Resonance Imaging) according to claim 1, wherein the supporting bench has a height such that when the patient support is mounted on the supporting bench, the patient support has a normal sitting height for a person.

* * * * *